United States Patent

Malin et al.

[11] Patent Number: 5,084,007
[45] Date of Patent: Jan. 28, 1992

[54] METHOD FOR CHEMICAL PROMOTION OF THE EFFECTS OF LOW CURRENT TRANSCRANIAL ELECTROSTIMULATION

[76] Inventors: David H. Malin, 1610 Wavecrest La., Houston, Tex. 77062; Malcolm H. Skolnick, 733 Brogden Rd., Houston, Tex. 77024

[21] Appl. No.: 652,876

[22] Filed: Feb. 8, 1991

Related U.S. Application Data

[63] Continuation-in-part of Ser. No. 392,868, Aug. 11, 1989, abandoned.

[51] Int. Cl.$^5$ ............................ A61N 1/30; A61N 1/00
[52] U.S. Cl. ........................................ 604/20; 128/421
[58] Field of Search .................. 604/20; 128/783, 789, 128/791, 419 R, 421; 606/32

[56] References Cited

U.S. PATENT DOCUMENTS

| | | | |
|---|---|---|---|
| 4,233,986 | 11/1980 | Tannenbaum | 128/421 |
| 4,294,245 | 10/1981 | Bussey | 128/421 |
| 4,331,145 | 5/1982 | Winter | 604/20 |
| 4,439,452 | 3/1984 | Ehrenpreis et al. | |
| 4,509,521 | 4/1985 | Barry | 128/421 |
| 4,646,744 | 3/1987 | Capel | |
| 4,702,254 | 10/1987 | Zabara | 128/421 |
| 4,724,841 | 2/1988 | Kastrubin et al. | 128/421 |
| 4,779,044 | 10/1988 | Skolnick et al. | |
| 4,784,142 | 11/1988 | Liss et al. | 128/421 |
| 4,844,075 | 7/1989 | Liss et al. | 128/419 R |
| 4,856,526 | 8/1989 | Liss et al. | 128/422 |
| 4,865,048 | 9/1989 | Eckerson | 128/421 |

FOREIGN PATENT DOCUMENTS

| | | | |
|---|---|---|---|
| 1205916 | 1/1986 | U.S.S.R. | 604/20 |
| 1279640 | 12/1986 | U.S.S.R. | 128/421 |
| 1318236 | 6/1987 | U.S.S.R. | 604/20 |
| 1410992 | 7/1988 | U.S.S.R. | 604/20 |
| 0000063 | 1/1987 | World Int. Prop. O. | 128/421 |

OTHER PUBLICATIONS

Wilson, Lawrence F., et al., "Cranial Electrotherapy Stimulation for Attention-to-Task Deficit: A Case Study", Am. J. Electromedicine 93-98 (Dec. 1988).

Duarte, G. I. B. P., et al., "Isolation and Characterization of Human Brain Aminopeptidase which Hydrolysis [sic] Enkephalin-Containing Peptides", 12 Neuropeptides 67-73 (1988).

Qiao, J-T., et al., "Dorsal Raphe and External Electrical Stimulation Modulate Noxious Input to Single Neurons in Nucleus Parafasicularis Thalami", 21 Brain Res. Bull. 671-675 (1988).

Malin, D. H., et al., "Auricular Microelectrostimulation: Naloxone-Reversible Attenuation of Opiate Abstinence Syndrome", 24 Biol. Psychiatry 886-890 (1988).

Hymel, C., et al., "Transcranial Electrostimulation Energy Density Distribution in the Brain and Effects on Somatosensory and Limbic Nuclei", Abstract presented at Nov. 13-18, 1988 Annual Meeting, Society for Neuroscience (1988).

Ellison, F., et al., "Opiate Withdrawal and Electrostimulation", 13 L'Encephale 225-229 (1987).

Schmitt, R., et al., "Cranial Electrotherapy Stimulation as a Treatment for Anxiety in Chemically Dependent Persons", 10 Alcoholism: Clinical Exper. Res. 158-160 (1986).

Jarzembski, W. B., "Electrical Stimulation and Substance Abuse Treatment", 7 Neurobehavioral Toxicol. Terat. 119-123 (1985).

*Primary Examiner*—C. Fred Rosenbaum
*Assistant Examiner*—Sharon Finkel
*Attorney, Agent, or Firm*—Vaden, Eickenroht, Thompson & Boulware

[57] ABSTRACT

Method of providing relief from painful or stressful stimuli, or remediating imbalances or deficiencies in the neuroactive substances that modulate neurohumoral mechanisms, which involves concomitant administration of a neuroactive chemical promoter and transcranial electrostimulation. This combination enhances the ability of the central nervous system to provide relief from, for instance, pain, addiction withdrawal, anxiety and depression.

27 Claims, 3 Drawing Sheets (List continued on next page.)

** $p < .01$ vs all other groups

Prieurm G., et al., "Approche Mathématique de l'action Biologique des Courants de Limoge", 9 J. Biophysique et Biomèchanique 67-74 (1985).

Senior, J. E., "The Elusive Search for Electroanesthesia", 19 Medical Instrumentation 86-87 (1984).

"Cranial Electrostimulation", 251 JAMA 1094 (1984).

Schmitt, R., et al., "Cranial Electrotherapy Stimulation Treatment of Cognitive Brain Dysfunction in Chemical Dependence", 45 J. Clin. Psychiatry 60-63 (1984).

Danguir, J. et al., "LCEC Monitoring of 5-Hydroxyindolic Compounds in the Cerebrospinal Fluid of the Rat Related to Sleep and Feeding", 8 Brain Res. Bull. 293-297 (1982).

Besson, J. M., "Analgesia Induced by Electrical Stimulation of the Brain Stem in Animals: Involvement of Serotonergic Mechanisms", 30 Acta Neurochirurgica, Suppl. 201-217 (1980).

Empson, J. A. C., "Does Electrosleep Induce Natural Sleep?", 35 Electroencephalography Clin. Neurophysiol. 663-664 (1973).

Advertising/Information Brochure, "CES Reduces Anxiety and Depression", thought to have been distributed by Neuro Systems, Inc. (Garland, Tex.), date unknown.

Chemical Abstracts, vol. 110, No. 23, Jun. 5, 1989, (Columbus, Ohio, U.S.), D. H. Malin, et al.,: "augmented analgesic effects of enkephalinase inhibitors combined with transcranial electrostimulation", see p. 64, abstract 205560u & Life Sci. 1989, 44(19), 1371-6 (Eng.).

Chemical Abstracts, vol. 113, No. 13, (Columbus, Ohio, U.S.), D. H. Malin, et al.: "Augmented analgesic effects of L-tryptophan combined with low current transcranial electrostimulation", see p. 73, abstract 10923k & Life Sci. 1990, 47(4), 263-7 (Eng.).

Murray, J. B., et al., "Transcranial Auricular Pain Sensitivity and Electrostimulation (TCET): Naloxone-Reversible Attenuation of Pain Sensitivity and Opiate Abstinence Syndrome", 13 (Part 2) Abst. Soc. Neuroscience 1304 (1987).

Smith, R. B., Cranial Electrotherapy Stimulation, in Neural Stimulation, vol. II, J. B. Myklebust, et al., eds., Boca Raton, Fla: CRC Press, pp. 129-150 (1985).

METHOD FOR CHEMICAL PROMOTION OF THE EFFECTS OF LOW CURRENT TRANSCRANIAL ELECTROSTIMULATION

This application is a continuation-in-part of co-pending application Ser. No. 07/392,868, filed on Aug. 11, 1989, now abandoned.

INTRODUCTION

1. Field of the Invention

The present invention relates to the concomitant administration of transcranial electrostimulation and chemical promoters to produce greater effects when acting together than either would produce acting individually. In more detail, the present invention relates to a method of medical treatment of a mammal which produces greater and longer lasting analgesic, anti-abstinence, anti-withdrawal, anti-anoxiant, anxiolytic, anti-psychotic, anti-depressant, relaxant, and anti-inflammatory effects than can be produced with drugs associated with these effects with the use of the same, or even lesser, dosages needed to achieve the effect.

2. Background of the Invention

Nerve cells, or neurons, are made up of a cell body, the perikaryon, and one or more long processes or extensions, axons and dendrites. The cell body can range in size from two to five hundred microns. For neurons with long and multiply branched axons and dendrites, the cell body may be a small fraction of the total neuron.

The axon is the longest process of the neuron. Some neurons may have axons as long as 25 cm. In most nerve cells, the axon transmits nerve impulses to the dendrites of the next neurons in line. The gap between the tip of the axon of one neuron and the adjacent cell is referred to as a synapse. The dendrites are shorter and more branched in structure than the axon and function as receivers. Axons can also transmit impulses to the cell body itself. Bundles of axons form nerves.

The ability of a neuron to respond to stimuli by generating synaptic or action potentials comes from special properties of its membrane. The total surface of the neuronal membrane, although greatly varying over the range of cell types, tends to be very large. Some neurons have less than 5 percent of their surface area in the cell body itself; filamentous processes extending from the perkaryon account for the rest. The processes-dendrites at the input end of the neuron and axons at the output end—not only extend the membrane but allow the maximum number of synaptic contacts to be made with other neurons.

Transmission of nerve impulses between neurons is an electrochemical process in which electrical impulses reaching the neuron's terminal cause various chemicals, referred to as neurotransmitters, to be emitted. Once released by the neuron, the neurotransmitter crosses the synapse (a gap of 20 nm) to the membrane of the next neuron in the neuronal circuit. There, the neurotransmitter interacts with specific receptors and generates a new electrical impulse, which continues the signal. The neuron sending a signal across the synaptic gap is called the presynaptic neuron. The receiving neuron is the postsynaptic neuron.

Alternatively, the chemical can be released into the general stream of extracellular fluid and subsequently join the flow of cerebrospinal fluid (CFS). The released chemical may simply interact locally with receptors on neurons in the immediate neighborhood (paracine action) or the chemical may travel further to interact with specific receptors positioned at relatively distant target sites, in adjacent brain regions or in other parts of the body (endocrine action).

The released chemicals mostly act simply as neurotransmitters, but a subcategory (which may be coreleased with the neurotransmitter) can also act as modulating agents (neuromodulators). These agents influence the extent to which their own, or adjacent, nerve terminals can either release, or respond to the action of, neurotransmitters. Released chemicals which travel to and act at other parts of the body are generally referred to as hormones.

Neuromodulation is one of the most important intrinsic properties of individual neurons. Neuromodulation is generally defined as the ability of neurons to alter their electrical properties in response to intracellular biochemical changes resulting from synaptic or hormonal stimulation. This property not only allows the nervous system to adapt its control of physiological functions to a continually changing environment, but also forms the basis for many long-lasting changes in human behavior and in the behavior of animals. Changes in behavior that can be related directly to changes in the electrical responses of specific neurons include the triggering of long-lasting, but relatively fixed and inate, behaviors such as feeding and reproduction, as well as alterations in behaviors that can be ascribed to learning.

It is these chemicals, and their effects on behaviors and nervous system functions, with which the present invention is concerned. Specifically, the present invention is concerned with the interaction of these chemicals with the effects of transcranial electrostimulation on the behaviors and the function of the nervous system. Transcranial electrostimulation, or TE, is described in detail in U.S. Pat. No. 4,646,744, and that description is incorporated herein in its entirety by this specific reference to that patent. In brief, TE may be described as the application of extremely low (on the order of 10 $\mu$A), pulsed, charge-balanced current across the head through electrodes of opposite polarity attached to low impedance sites on the head. The current levels applied are well below the current amplitudes commonly employed in electro-acupuncture, transcutaneous electrical nerve stimulation (TENS), and other electrostimulation techniques, and the waveform used is significantly different. Nevertheless, a growing body of scientific literature documents the effectiveness of TE in, for instance, inducing analgesia (Skolnick, M. H., et al., "Low current electrostimulation produces naloxone-reversible analgesia in rats," 13 Soc. Neurosci. Abstr. 1304 (1987)) and reducing the severity of opiate withdrawal syndrome (Murray, J. B., et al., "Transcranial auricular electrostimulation (TCET): Naloxone reversible attenuation of pain sensitivity and opiate abstinence syndrome," 13 Soc. Neurosci. Abstr. 1304 (1987)). These same references document the reversibility of these effects with exogenous naloxone, a potent inhibitor of the effects of endogenous opiates which exerts its effect by blocking the opiate receptors, suggesting strongly that TE effects are mediated by release of endogenous opioids. The references also provide evidence to indicate that TE is as potent an inductor of analgesia as focal (in brain electrodes) electrical stimulation (Dong, W. P., et al., "Effects of dorsal raphe, habenula and external stimulation on septal neurons in the rat", 14 Proc. Soc. Neurosci. 855 (1988)).

SUMMARY OF THE INVENTION

Surprisingly, however, and as will be shown by the experimental evidence set out below, it has been discovered that when various neuroactive chemical promoters are administered concomitantly with TE, a more intense and prolonged physiological result is achieved than was expected. The present invention may therefore be characterized broadly as a method medical treatment of a mammal involving the enhancing the normal efforts of the central nervous system to ameliorate or otherwise compensate for such stress as pain, anxiety, addiction withdrawal symptoms, depression, and inflammation, comprising the concomitant administration of a neuroactive chemical promoter and subsensory, transcranial electrostimulation.

The method of the present invention is also useful in remediating imbalances or deficiencies in levels of neuroactive substances that modulate neurohumoral mechanisms in living beings. Concomitant administration of TE and a neuroactive chemical promoter provides a treatment modality which can replenish, initiate or invigorate production of and/or compensate for, such deficiencies and/or imbalances.

Such methods are characterized by a number of advantages over previously available techniques. The ability to achieve analgesia to relieve chronic pain, to assist relaxation in combating stress related disorders and to ameliorate drug withdrawal syndromes with a non-addictive modality for which tolerance does not increase is of obvious clinical significance. Further, the method of the present invention is used to achieve the same effects as many specialized drugs, but with lower dosage levels or, in some cases, without even administering the drug (e.g., by accomplishing the same effect by using a different agent), therefore potentially decreasing the cost and/or side effects of drug therapy. Another significant advantage of the method of the present invention is that the ameliorative effects are not only more pronounced but of longer duration than the effects produced by administration of the drug alone. Such results can even be achieved using subclinical doses of the neuroactive chemical promoter.

It is, therefore, an object of the present invention to provide a method for use in, for instance:
(1) smoking cessation,
(2) withdrawal syndrome from addiction of, for instance, morphine, heroin and related narcotics, as well as other addictive drugs such as alcohol and cocaine,
(3) chronic pain resulting from, for instance, arthritis, migraine headaches, low back pain, failed surgery, terminal cancer, and other sources,
(4) acute pain,
(5) psychoses,
(6) depression,
(7) anxiety,
(8) thermal insult, and
(9) any of a host of stress-related disorders such as insomnia, certain forms of obesity and anorexia, post-traumatic stress disorder, and clinical depression.

Another object of the present invention is to provide a method of treating patients for stressful stimuli such as those listed in the preceding paragraph which promotes or enhances the normal mechanisms by which the patient's central nervous system ameliorates the effects of such stimuli.

Another object of the present invention is to provide an effective method for treating mammals experiencing stressful stimuli such as those listed above with the same or reduced dosages as currently used to achieve enhanced and/or prolonged effects.

Other objects of the present invention will be made clear to those skilled in the art by the following detailed description of several preferred protocols for practicing the method of the present invention. In setting out these descriptions, it is not intended that the invention be limited to these specific embodiments. These descriptions are instead set out herein for purposes of exemplification and to comply with the requirements of §112 of the Patent Statute.

DETAILED DESCRIPTION OF THE PREFERRED EMBODIMENTS

The reaction to and management of pain, stress and anxiety are modulated by a host of neurotransmitters synthesized and pharmacologically active in the mammalian brain and spinal chord. These endogenous transmitters are synthesized in various regions of the brain from various chemical precursors and are broken down or metabolized by enzyme systems at various sites in the central nervous system (CNS). Neurotransmitters have been shown to induce or be involved with analgesic, anxiolytic, sedative, hypnotic, CNS depressant, and psychotropic effects.

A variety of chemical agents have been discovered which interact with neurotransmitter systems of the CNS. These agents may, for instance, possess a chemical structure which mimics a particular transmitter or class of transmitters and which binds to the cellular receptors uniquely associated with the transmitter family. For example, exogenous heroin or morphine cross the blood-brain barrier and displace the brain's endogenous peptidyl opiates, the endorphins and enkephalins.

These chemical agents, referred to generally herein as neuroactive chemical promoters, include any substances which are capable of exerting an effect on the CNS which enhances the capacity of the CNS to relieve or ameliorate the effects of such stressful stimuli as pain, addiction withdrawal syndrome, and so on as listed above, or which are beneficial in remediating imbalances or deficiencies in the endogeneous neuroactive substances that modulate neurohumoral mechanisms. These neuroactive chemical promoters may include, but are not limited to, hormones such as α-melanocytestimulating hormone (MSH) and adrenocorticotropin (ACTH), synthetic derivatives of such opioid peptides as leu- and met-enkephalin and β-endorphin which are more stable metabolically, e.g., less susceptible to degradation by non-specific amino- and carboxypeptidases or such enzymes as the enkephalinases, than the naturally-occurring opioid peptides, for instance, those synthetic derivatives made by substitution of an amide group to form met-enkephalin amide, by replacing a glycine residue of met- or leu-enkephalin with D-alanine, or the carbinol derivative of met-enkephalin known as FK33-824, precursors of various endorphins, dynorphins, and enkephalins such as B-lipotropis pro-opiomelanocortin, pro-enkephalin A and pro-enkephalin B (pro-dynorphin), enzymes active in the metabolic pathways involved in production or degradation of the above-listed endorphins, dynorphins and enkephalins such as endorphinase, enkephalinase, and carboxypeptidases, inhibitors of the enzymes active in the metabolic pathways involved in production or degradation of endorphins, dynorphins, or enkephalins such as acetorphan, thiorphan and kelatorphan, a D-form amino acid such as D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine, and D-valine, or a di- or tri-peptide comprised of any one or more of these D-form amino acids, amino acid derivatives such as 3-aminotyrosine, a thiol benzyl amino acid such as (2-[mercapto-3-phenyl-propanol]-L-leucine or any N-[(R,S)-2-carbethoxy-3-phenyl-propanol]-L-leucine, a carboxyalkyl methylester, hydrocinnamic acid or other propionic acid derivative such as ibuprofen, naproxen, and piroxicam, a barbituate such as secobarbital, amobarbital, and pentobarbital, pyrophosphate, 0-phenanthroline, phosphamidon, Z-leucine-NHOH, Z-glycine-NHOH or an antibiotic such as bacitracin, bestatin, or puromycin, indoleamines such as serotonin, tryptophan, tryptamine, histamine, melatonin, indoleacetic acid, 5-hydroxytryptophan, (N')-methyl and (N')-acetylserotonin, N,N-dimethyl tryptamine (DMT), bufotenine, psilocine, psilocybin, and other derivatives of tryptamine, enzymes active in the metabolic pathways involved in production and degradation of indoleamines such as 5-hydroxytryptophan decarboxylase, tryptophan 5-monoxygenase, monoamine oxidase, and tryptophan hydroxylase, inhibitors of the enzymes active in the metabolic pathways involved in production and degradation of indoleamines such as p-chlorophenylalanine, 5-hydroxytryptophan antagonists such as those described in U.S. Pat. No. 4,963,546, North, et al., the ergot alkaloids such as lysergic acid diethylamide (LSD) and methysergide (generally in the form of methysergide maleate), H₁ blockers of the ethylenediamine type, various indole compounds, spiroperidol, pirenperone, cyproheptadine, phenothizaines such as chlorpromazine, β-haloalkylamines such as phenoxybenzamine, siperone, metergoline, metitepine, mianserin, pizotyline (pizotifen), cinanserin, and ketanserin, and substances such as clomipramine and fluoxetine which inhibit uptake, catecholamines such as noradrenalin, adrenalin, dopamine, 3,4-dihydroxyphenylalanine (dopa), normetanephrine and metanephrine, enzymes active in the metabolic pathways involved in production or degradation of catecholamines such as monoamine oxidase, catechol-0-methyltransferase, dopamine β-hydroxylase, phenylethanolamine-N-methyltransferase, and tyrosine-3-monooxygenase, inhibitors of the enzymes active in the metabolic pathways involved in production and degradation of catecholamines such as pargyline, nialamide, and tetrahydrobiopterin, catecholamine agonists and antagonists such as the phenothiazones, thioxanthenes, and butyrophenones, isoproterenol, prazosin, rauwolscine, yohimbine, metoprolol, proctolol, butoxamine, cocaine, imipramine and other tricyclic antidepressants, guanethidine, bretylium, sympathomimetic drugs such as tyramine and ephedrine, and agents which inhibit catecholamine storage such as reserpine, tetrabenazine and α-methyl-m-tyrosine amino acids present in the central nervous system such as gamma-aminobutyrate (GABA), glycine, glutamate and aspartate, those amino acids capable of inducing central nervous system response such as β-alanine and taurine, and combinations of amino acids such as D-phenylalanine and D-leucine and combinations of amino acids and an aspirin-like drug such as D-phenylalanine and an antipyretic, anti-inflammatory analgesic, both as described in U.S. Pat. No. 4,439,452, Ehrenpreis, et al., enzymes active in the metabolic pathways involved in production and degradation of these amino acids such as glutamate decarboxylase, inhibitors of the enzymes active in the meta bolic pathways involved in production and degradation of these amino acids, amino acid antagonists and/or binding competitors such as bicuculline, picrotoxin, apiamine, strychnine, glutamate diethylester, alphaamino adipate, 2-amino-5-phosphonovalerate and lactonized kainate, agents that mimic the action of these amino acids such as muscimol or inhibit the re-uptake of the amino acid such as 2,4-diaminobutyrate, nipecotic acid, guvacine, and 2-hydroxy-γ-aminobutyrate, agents which alter the rate of synthesis or degradation of the amino acid such as aminooxyacetic acid or which potentiate the response to the amino acid such as the benzodiazepines diazepam, clordiazepocide, clorazepate, and flurazepam, a variety of peptides either found in the central nervous system or which are capable of exerting various effects on the CNS including carnosine, homocarnosine, anserine, pyroglutamylhistidylprolinamide, adrenocorticotropin hormone (ACTH), cholecystokinin, somatostatin, substance P, scotophobin, gastrin, vasopressin, oxytocin, vasoactive intestinal peptide (VIP), glucagon, thyrotropin releasing hormone, and secretin, enzymes active in the metabolic pathways involved in production and degradation of the above-listed peptides, such as carnosine synthetase, inhibitors of the enzymes active in the metabolic pathways involved in production and degradation of the above-listed peptides, and antagonists of the above-listed peptides, e.g., cholecystokinin, such as proglumide and lorglumide, cholinergic agents such as acetylcholine, enzymes active in the metabolic pathways involved in production and degradation of cholinergic agents such as acetylcholinesterase, choline acetyltransterase or butyrylcholinesterase, inhibitors of the enzymes active in the meta bolic pathways involved in production and degradation of cholinergic agents, antagonists of the enzymes active in the metabolic pathways involved in production and degradation of cholinergic agents and substances which block the uptake of such agents such as methacholine, nicotine, physostigmine, or diisopropyl phosphorofluoridate.

In addition to the substances listed above, the phrase "neuroactive chemical promoter" is intended to include a large number of substances which are not necessarily easily classified into one of the above groupings but which nonetheless are capable of exerting an effect on the central nervous system which enhances the capacity of CNS to relieve or ameliorate the effects of, for instance, the above-listed stressful stimuli. Such substances can best be described by citation to a reference characterized the substance in detail as follows:

pyrido[2,3-e]-as-triazine derivatives as described in U.S. Pat. No. 4,324,786, Messmer, heteramino benzofurans as described in U.S. Pat. No. 4,451,462, Wenk, isochromans as described in U.S. Pat. No. 4,487,774, McCall, 4,5 α epoxymorphinan-6-spiro-2'-(4'-carboxy,1',3'-thiazolindine) derivatives as described in U.S. Pat. No. 4,496,570, Bodor, pyrazolo/4,3-C/pyridines as described in U.S. Pat. No. 4,500,525, Winters, imidazo[1,2-A]pyridine derivatives as described in U.S. Pat. No. 4,501,745, Kaplan, et al., 2-benzoxepins as described in U.S. Pat. No. 4,556,656, McCall, pyrazolo[1,5-a]pyrimidines as described in U.S. Pat. No. 4,576,943, Tomcufcik, et al., bridged pyridines as described in U.S. Pat. No. 4,587,253, Halczenko, et al., condensed pyrrolinone derivatives as described in U.S. Pat. No. 4,590,189, Hiraga, et al., 6-fluoro-3-[3-(1-heterocyclo)-propyl]-1,2-benzisoxazoles as described in U.S. Pat. No. 4,591,586, Davis, et al., 8-[3-(4-amino carbonyl piperazino and piperidino propyl]xanthenes as described in U.S. Pat. No. 4,599,338, Regnier, et al., substituted and bridged pyridines as described in U.S. Pat. No. 4,599,341, Halczenko, et al., 2-(arylalkyloxymethyl)morpholines as described in U.S. Pat. No. 4,605,654, Cousse, et al., benzofuran- and benzopyran-carboxamide derivatives as described in U.S. Pat. No. 4,617,714, Tahara, et al., heterocyclic derivatives bearing an amino radical as described in U.S. Pat. No. 4,647,557, Moinet, et al., 3-amino-2,3-dihydro-1-benzoxepines as described in U.S. Pat. No. 4,672,062, Ohlendorf, et al., fused imidazoheterocyclic compounds as described in U.S. Pat. No. 4,772,600, Tomczuk, et al., 3,6-disubstituted trizolo[3,4-A]phthalazine derivates as described in U.S. Pat. No. 4,783,461, Occelli, et al., 1,3-dithiolano-,1,4-dithiino- and 1,4-dithiepino[2,3-C]pyrrole derivatives as described in U.S. Pat. No. 4,788,191, Hiraga et al., and 1,2,3,3A,8,8A-hexahydro-3A,8(and) 1,3A,8-di(and tri)methylpyrrolo(2,3-B) indoles as described in U.S. Pat. No. 4,791,107, Hamer, et al.

phenthiazine compounds as described in U.S. Pat. No. 2,837,518, Jacob, et al.

In spite of the length of the above list of patents, it is not intended that the present invention be limited to the substances described therein. There are many more substances included within the scope of the phrase neuroactive chemical promoters; space, practicality, and the time available for developing a longer list, as well as the requirement of the Patent Statute that the invention need only be exemplified, augur against developing such a list.

As noted above, transcranial electrostimulation (TE) is described in U.S. Pat. No. 4,646,744, incorporated herein by reference. However, once again, it is not intended that the method of the present invention be limited only to that which is set out in that patent. Actual experimental protocols are set out below, but in general, TE can be described as the application of a continuous series of sub-sensory electrical pulses from one side of the patient's head to the other through electrodes of opposite polarity affixed to the patient's head. Extensive experimentation has shown that those sites on the head having the relatively lowest impedance are the best sites for placement of the electrodes in that they are more effective in inducing a response. Further, the impedance must be low enough in an absolute sense to make it possible to achieve the desired current level (see below) at a voltage which is below the threshold of detection by the patient. In both humans and laboratory animals, it is particularly preferred that the electrodes be affixed to the external ears, or pinnae; however, the mastoid process has also been used to advantage on human patients. On the ear, as is the case for other locations on the head, a change in position of as little as two millimeters can make significant differences in impedance; preferred sites in humans are the ear lobe, inner ear and upper ear, on rats, the base of the ear and the apex of the antihelix are preferred.

Experimentation has also shown that stimulus sessions of about 30 minutes in small animals such as rats and 45 minutes in humans produce effects which persist for three or more hours. The optimum frequency is approximately 10 Hz, and the optimum current is in the range of about 5 to about 25 $\mu$A, and in humans, from about 10 $\mu$A to about 40 $\mu$A. Further, the results are generally improved when biphasic waveforms are used to deliver a charge-balanced current rather than monophasic, non-charge balanced waveforms. The phrase "biphasic, charge-balanced waveform" refers to a series of generally rectangular pulses having, for instance, approximately a 10 $\mu$A, 2.0 msec positive phase separated by 98.0 msec negative phases having an amplitude of approximately 0.2 $\mu$A. It is not intended, however, that the method of the present invention be practiced only using those parameters. Satisfactory results can be obtained by varying these parameters as follows:

| | |
|---|---|
| pulse width (duration) | about 0.1–about 8.0 msec |
| frequency | about 5–about 50 Hz |
| current | about 5–about 40 μA |
| duration | about 10–about 60 min. |

Further, monophasic, non-charge balanced waveforms, although not as efficacious as biphasic charge balanced waveforms, may also be used to advantage by varying the parameters within these same ranges.

The method of the present invention may be better understood by reference to the following examples of several presently preferred embodiments thereof.

EXAMPLE 1

Effect of Amplitude, Frequency, Duration and Repeated Stimulation

Three hundred and thirty four male Sprague-Dawley rats weighing between 180 and 210 grams were used. The animals were housed in groups of four with ad lib food and water and a 12 hour alternating light/dark cycle. All animals were naive in the sense that they had no previous experience with TE; however, a day prior to each experiment, the subjects were placed in restraints for one hour to acclimate them to the experimental conditions.

Animals were anesthetized by injection of 400 mg/kg chloral hydrate i.p. Gold plated stainless steel electrodes (cosmeticians' ear piercing studs) were inserted bilaterally into the pinnae at the apex of the antihelix. This site was chosen because it resulted in a relatively lower ear to ear impedance of $8.0 \pm 0.4$K ohms (n=26) as measured with a Grass impedance meter.

A computer controlled stimulator was used to produce a continuous series of biphasic, charge balanced, rectangular pulses which, unless otherwise specified, had a repetition rate or 10 Hz, first phase amplitude of 10 μA, and first phase duration of 0.1 msec. The second phase duration was approximately equal to the interval between consecutive first phases, and the amplitude such that the net charge delivered in any cycle was zero. An essentially constant current was maintained by the stimulator during each phase, irrespective of variations in the rat impedance.

Fifteen minutes prior to stimulation, the rats were placed in adjustable cylindrical plastic restrainers. Leads with a 200 K ohm resistor in series were connected to the electrodes, with the positive lead (that delivering a positive first phase) attached to the animals' right ears. Each experiment included a "sham control group" consisting of rats which were implanted, restrained and connected as above, but which did not receive any electrical stimulation.

All observations were carried out by operators who were blind to the stimulus parameters and to the identity of sham treated animals. Care was taken to exclude systematic influences on the arising from stimulation at different times of day by treating and testing equal numbers of animals from each stimulation or sham group in each stimulation session.

Analgesia was assessed using the wet tail flick method described in Mitchell, D. and R. F. Hellon, "Neuronal and behavioral response in rats during noxious stimulation of the tail," Proc. Royal Soc. (Lond.) 169–194 (1977). Immediately preceding and following electrostimulation, the terminal one inch of each rat's tail was immersed in water at 50° C. The time in seconds measured with a stopwatch from submergence to the first flicking response was taken as the tail flick latency. If a rat did not respond within 20 seconds, its tail was removed from the water to prevent tissue damage. The baseline (pre-stimulation) tail flick latency established by using a 50° C. water bath was $6.39 \pm 0.07$ seconds (n=292). Four successive latencies were determined during both the pre- and post-test; in each case, the first measurement was discarded and the last three were averaged to yield pre- and post-stimulation scores. Each rat's analgesia rating was its mean post-test latency minus its mean pre-test latency. Results may be summarized as follows.

One-way analysis of variance indicates a significant effect of amplitude on change in tail flick latency (measured at 30 mins. of 10 Hz, 0.1 msec pulse width TE at 0, 5, 7.5, 10, 12.5, 15, and 20 μA), $F(6,161)=2.32$, $p<0.02$, according to Dunnett's Test for multiple comparisons with a single control group.

The results of the experiment varying the duration of electrostimulation indicate that thirty minutes (as compared 1, 10, 20, 40, 50 and 60 minutes with 0.1 msec, 10 Hz, 10 μA TE) of TE resulted in the greatest increase in tail flick latency ($1.92 \pm 0.20$ seconds). One way analysis of variance reveals a significant effect of stimulation duration on change in tail flick latency, $F(6,63)=3.43$, $p<0.005$. Dunnett's test for multiple comparisons with a single control group indicated that only the group receiving 30 minutes of TE differed significantly from the sham treated controls, $p<0.05$. The group receiving 50 minutes of stimulation closely approached a significant difference from controls, $p<0.10$.

Upon measuring the duration of analgesia, it was found that the electrostimulated rats show greater latency increases from pretest than sham treated controls at all times tested (0, 40, 80, 120, 160 and 200 mins. after 30 minutes of sham or 0.1 msec, 10 Hz, 10 μA TE) reaching a peak 40 minutes after the end of stimulation. Two way analysis of variance with one repeated measures variable reveals a significant effect of TE (stimulation vs. sham), $F(1,22)=32.30$, $p<0.01$, and a significant, $F(5,110)=2.32$ (ns), indicating that differences between treated and sham groups did not change significantly over 200 minutes. Post hoc comparisons using Tukey's HSD test reveal significant differences between stimulated and sham groups at every time interval. At 120 and 160 minutes post stimulation, the difference between groups was significant at the $p<0.05$ level. At all other intervals, the difference between groups was significant at the $p<0.01$ level. The TE treated animals had significantly higher latency increases over pretest at 40 minutes, $p<0.05$, than at 80, 120, 160 or 200 minutes. Latency increases were significantly higher, $p<0.05$, immediately following TE than at 120, 160 or 200 minutes after stimulation.

The effects of repeated daily electrostimulation were investigated by analysis of variance with one repeated measured variable, which revealed a highly significant effect of TE (stimulation vs. sham), $F(1,28)=94.29$, $p<0.001$, between rats receiving five daily 30 min. sham sessions and five daily 30 minute sessions of 0.1 msec, 10 Hz, 10 μA TE. The time effect (days one through five) was not significant, $F(4,112)=1.45$ (ns). The interaction effect (TE×days) was also not significant, $F(4,112)=1.81$ (ns), indicating that the effect of electrostimulation vs. sham did not change significantly over five days. Post hoc comparisons using Tukey's HSD test revealed significant differences, $p<0.05$ between stimulated and sham animals on each day except the second.

EXAMPLE 2

Effect of Pulse Width, Frequency, Polarity Charge Balance and Monolateral Stimulation Mice were kept and subjected to the same preinvestigational regimens as described in Example 1 (N=189). For monolateral experiments, the studs were inserted into either the right or left ear only. An essentially constant (±2%) stimulus current was maintained by connecting the constant voltage waveform generator in series with a 200 K ohm resistor.

Experiment 1 tested the analgesic effects of different stimulus pulse widths in 63 rats not previously exposed to TE that were randomly assigned to seven groups of 9 rats each. These groups had 30 minutes of 10 $\mu$A, 10 Hz stimulation with, respectively, 0 (sham), 0.1, 0.5, 1, 2, 4 and 8 msec first phase pulse widths. As in all the following experiments, tail flick latencies (TFLs) were determined before and after stimulus by an operator who was blind to the stimulus parameters, and the time difference in seconds determined the animals' analgesia scores.

Experiment 2 tested the analgesic effects of different stimulus frequencies in 63 rats were randomly assigned to seven groups of 9 rats each. These groups had 30 minutes of 10 $\mu$A, 2 msec pulse width stimulation at 0 (sham), 5, 7.5, 10.0, 15, 20, and 50 Hz.

Experiment 3 tested the necessity of using a charge balanced stimulus waveform in 27 rats randomly assigned to 3 groups of 9 rats each. These groups had 30 minutes of stimulus with, respectively, no stimulus waveform (sham); 10 Hz, 2 msec, 10 $\mu$A stimulation with a charge balanced waveform; or 10 Hz, 2 msec, 10 $\mu$A stimulation with a monophasic (non charge-balanced) waveform.

Experiment 4 tested the effect of stimulus polarity on the analgesia produced by TE in 15 rats tested three times in a blind, triple crossover design with 30-minute stimulus sessions. Each rat received a session of sham stimulation; one of 10 Hz, 2 msec, 10 $\mu$A charge balanced TE with standard polarity (positive lead on the right ear); and one of 10 Hz, 2 msec, 10 $\mu$A TE with reversed polarity (positive lead on the left ear). TFL analgesia scores in this experiment were determined in all animals before and after each session. Statistically weak results led to a repeat of the experiment using a further 12 subjects in the sample triple crossover design.

Experiment 5 investigated the efficacy of several electrode positioning schemes in 36 rats randomly assigned to three groups of 12 rats each. One group had one electrode in each ear, the other two groups had two electrodes in either the left or the right ear as described. Each animal had 30 minutes of 10 Hz, 2 msec, 10 $\mu$A charge balanced TE. TFL analgesia scores were determined in the usual way under blind conditions.

A one-way analysis of variance with the data from Experiment 1 indicates a significant effect for pulse width on the change in tail flick latency, $F(6,56)=2.283$, $p<0.05$. According to Dunnett's test for multiple comparisons with a single control, three groups (1, 2, and 8 msec pulse widths) differed significantly from the sham group in post hoc comparison, $p<0.05$. Although the 2 msec group showed the greatest overall degree of analgesia, the difference between this group and the 1 or 8 msec groups was not statistically significant.

The results of Experiment 2, varying frequency of electrostimulation, indicated that the 10 Hz group showed the greatest increase, 45%, in tail flick latency (2.28±0.61 sec). A one-way analysis of variance reveals a significant effect of electrostimulation frequency on the change in tail flick latency, $F(6,56)=4.012$, $p<0.002$. Post hoc comparisons using Tukey's HSD test show that only the 10 Hz group differed significantly from the sham controls, $p<0.05$.

The results of Experiment 3, effect of charge balance on changes in tail flick latency, demonstrate that the greatest increase in latency (2.95±0.43 sec), which represents a 49% increase in response time, occurred in the rats given charge balanced stimulation. A one-way analysis of variance shows a significant effect for both mono- and bipolar stimulation on the change in tail flick latency, $F(2,24)=13.703$, $p<0.001$. Post hoc comparisons using Tukey's HSD test indicate that both stimulus groups, regardless of charge compensation, were significantly different from sham, $p<0.01$. Although the biphasically stimulated group showed a TFL increase averaging 1 sec more than the monophasically stimulated group, this difference was not statistically significant.

Experiment 4 was initially conducted with a group of 15 animals, and a one-way analysis of variance indicated a significant effect of stimulation, $F(2,28)=4.579$, $p<0.02$. Comparison with Tukey's HSD test revealed that the group receiving positive stimulation on the right ear had a significant increase in TFL compared to sham, $p<0.05$. However, the reverse polarity group did not differ significantly with respect to either positive treatment or sham groups. The experiment was repeated with a further 12 rats. In the second experiment, one-way analysis of variance also indicated a significant effect of stimulation, $F(2,22)=7.546$, $p<0.003$. Comparison with Tukey's HSD test revealed a significant difference between positive and sham groups, $p<0.01$, and also between positive and reverse polarity groups, $p<0.05$. Analysis of the combined results from both groups (n=27) indicated a highly significant difference between positive polarity and sham, $p<0.01$, and between positive polarity and reverse polarity, $p<0.01$. In neither of the two polarity experiments, nor in the combined results, did the reverse polarity group differ significantly from sham.

The results of Experiment 5, which tested the effect of various electrode placements, indicates a significant effect of electrode placement, $F(2,33)$ 5.945, $p<0.01$ by one-way analysis of variance. Post hoc comparison using Tukey's HSD test indicates a significant difference with the group receiving standard electrode placement showing an increased TFL compared with either of the monolateral stimulation groups, $p<0.05$.

EXAMPLE 3

Effect of 5-HTP Administration and Inhibition of Enzymes Involved in Making Serotonin An experiment designed to assess the effect of concomitant administration of the precursor of the neuroactive chemical promoter serotonin, 5-HTP, and subsensory, transcranial electrostimulation was conducted as follows. Ninety-two male Simonsen Albino rats (Simonsen Laboratories, Inc., Gilroy, CA) weighing between 200 and 250 g at the time of testing were housed in groups of six with food and water available ad lib and on a 12/12 light/dark cycle. They were handled three minutes per day for 42 days and then restrained 10 minutes for the following three days. Electrodes were implanted as described in Example 1, and electronics were as described in Example 2.

Fifteen minutes prior to stimulation, the rats were placed in adjustable cylindrical plastic restrainers. Leads were connected to the electrodes with the positive lead (that delivering a positive first phase) attached the animals' right ears. Each experiment included a sham control group consisting of rats which were implanted, restrained and connected as above, but which did not receive any electrical stimulation.

All observations were carried out by operators who were blind to the stimulus parameters and to the identity of animals receiving stimulation. Care was taken to exclude systematic influences on the data arising from stimulation at different times of day by stimulating and testing equal numbers of animals from each stimulus or sham group in every stimulation session.

The rats were pretreated with dl-p-chlorophenylalanine, methyl ester (pCPA), Sigma Chemical Co. (300 mg/kg i.p.) dissolved in 2.0 ml of saline or with saline vehicle 48 hours prior to testing, and were also treated with either 5-hydroxy-dl-tryptophan, ethyl ester, (5HTP) Sigma Chemical Co. (100 mg/kg i.p.) dissolved in 1.5 ml. of saline in a 37° C water bath or with saline vehicle 30 minutes prior to testing. At that time the rats were placed in the cylindrical plastic restrainers and the elctrodes attached as described above. They then received 30 minutes of either TE or sham TE treatment (Table I).

TABLE I

Rats were assigned to the following treatment groups:

| TE GROUP TREATMENT | SHAM GROUP TREATMENT |
|---|---|
| A pCPA + 5-HTP | E pCPA + 5-HTP |
| B pCPA + Saline | F pCPA + Saline |
| C Saline + 5-HTP | G Saline + 5-HTP |
| D Saline + Saline | H Saline + Saline |

Analgesia was assessed using a pressure technique modified from that described by Randall, L. O. and J. J. Selitto, III Arch. Int. Pharmocodyn. 409–419 (1957). Each rat's tail was subjected to pressure (¼ inch from the tip) exerted by a metal wedge mounted on the end of a syringe which was pneumatically driven. The amount of pressure withstood by the rat was read from a mercury manometer as the rat made the first coordinated motor response to remove its tail. One experimenter operated the wedge and cut off air pressure when the rat responded as the other experimenters read the height reached by the mercury on the manometer. This pressure reading averaged over four trials was taken as the mean tolerated peak pressure (TPP). The difference in mean TPP, before and after TE, was taken as a measure of analgesia. Pressures values are expressed as mm of mercury (Hg) ±standard error.

Figure 1:
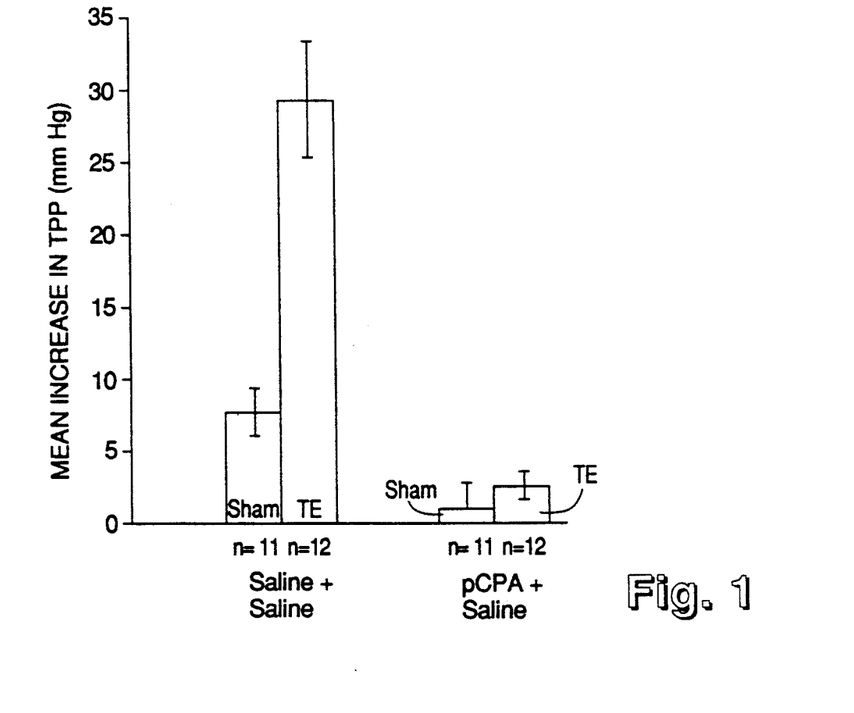
FIG. 1 is a bar graph showing the decreased TE-induced analgesia resulting from administration of p-chlorophenylalanine (pCPA), which depletes serotonin levels, in rats as described in Example 3, below.

TE treatment resulted in increased tolerated peak tail pressure. Considering all TE treated groups (Groups A–D, Table I), the average tolerated peak tail pressure was 18.2 mm Hg or 613 percent higher than in the sham treated groups collectively (p<0.001, FIGS. 1,2). The saline-TE treated group (Group D, Table I) tolerated an average of 29 mm Hg more peak pressure than did the saline-sham TE group (Group H, Table I). Treatment with pCPA diminished TE induced analgesia. While saline-TE treated rats (Group D, Table I) tolerated an average of 29.3±4.0 mm Hg, pCPA-TE treated rats (Group B, Table I) tolerated only 2.5±1.0 mm Hg, (a decrease of 91.5 percent (p<0.001, FIG. 1).

Figure 2:
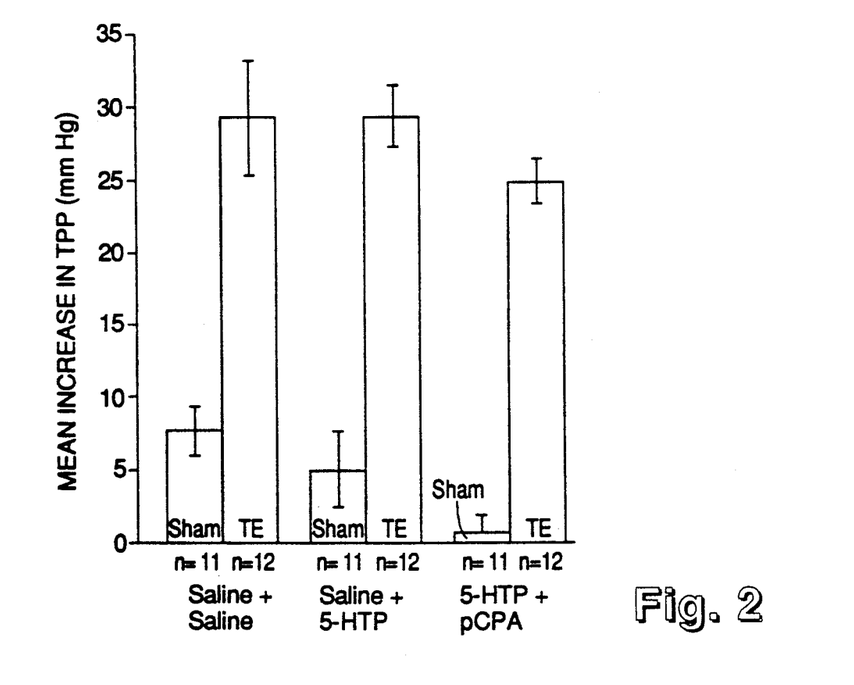
FIG. 2 is a bar graph showing the restoration of TE-induced analgesia after restoring serotonin levels to pCPA-treated rats by administering exogenous serotonin as described in Example 3, below.

Further treatment of pCPA treated rats with 5HTP resulted in saline control values of TE induced analgesia (FIG. 2). Neither the values of the pCPA-5HTP treated rats (25.4±1.7 mm Hg; Group A, Table I) nor those of the saline-5HTP treated rats (29.8±2.1; Group C, Table I) differed significantly from the TPP values of the saline-TE treated rats (29.3±4.0; Group D, Table I). Among the sham treated groups, the pCPA-saline (Group F, Table I) and pCPA-5HTP (Group E, Table I) group values were low compared with the saline-saline (Group H, Table I) group values, but the difference fell short of statistical significance.

EXAMPLE 4

Combined Effects of Transcranial Electrostimulation and i.c.v. Thiorphan

An experiment was conducted in which the combined effect of TE and the enkephalinase inhibitor thiorphan was assessed on analgesia. The subjects were 20 male Sprague-Dawley rats, weighing 200–225 grams. Subjects were maintained on ad lib food and water and a 12 hour light/dark cycle. Seven days prior to the experiment, each rat was placed under Innovar (tm) anesthesia, implanted with gold-plated stainless steel electrodes through the apex of the anti-helix of each pinna as described in Example 2, and stereotaxically cannulated in the third ventricle. Each cannula placement was subsequently confirmed by dye injection and histological examination. On the two days preceding the experiment, each rat was habituated to a cylindrical plastic restrainer.

Each rat was placed in the restrainer and pretested for nociceptive sensitivity by measurement of tail flick latency on the 50° C wet tail flick test (average of three trials). The ear electrodes of each rat were then connected to the stimulator through leads with a 200 K ohm resistor in series. Ten rats then received 30 minutes of TE stimulation (10 Hz, 10 µA, 2 msec pulse width), while ten rats (the "sham stimulation group") received no stimulation.

Beginning concurrently with TE or sham stimulation, five rats from each group then received 250 µg thiorphan i.c.v. (Peninsula Laboratories) in saline with 3% ethanol. A motor driven syringe delivered a gradual infusion of 5 µl/min of 2.5 mg/ml thiorphan solution over a 20 minute period. Five rats from each group were infused only with the injection vehicle of 3% ethanol in saline. Immediately following drug and electrostimulation treatment, all rats were retested under "blind" conditions for tail flick latency. Each animal's analgesia score was the percentage increase in tail flick latency from pretest to posttest. These scores were analyzed by two-way analysis of variance. The group receiving combined thiorphan and TE treatment was compared with all other groups according to Dunnett's Procedure for post-hoc comparison of a single treatment group with all others.

Figure 3:
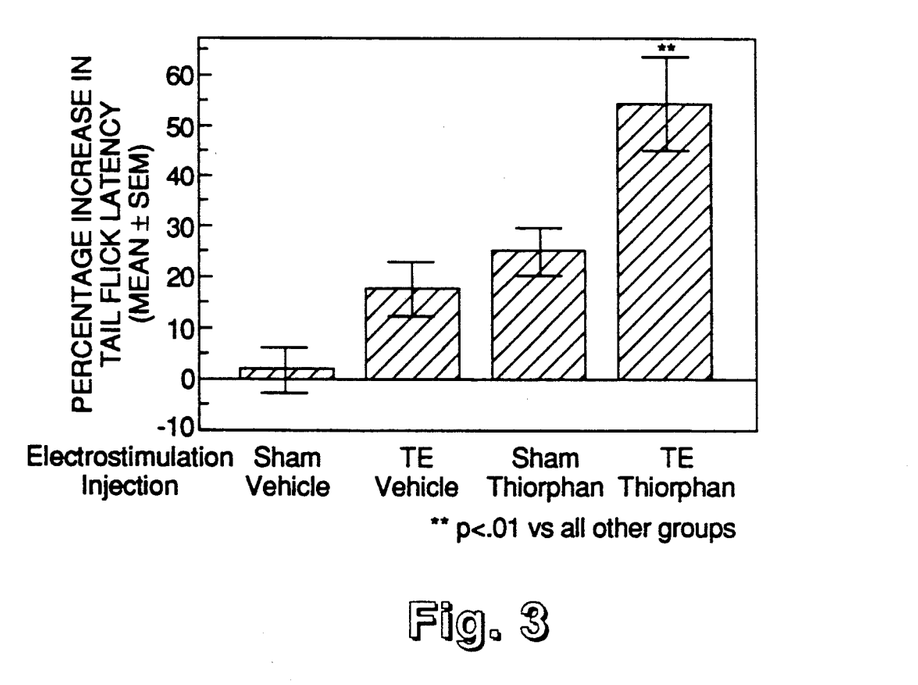
FIG. 3 is a bar graph showing the enhancement of TE-induced analgesia in rats by concomitant administration of thiorphan as described in Example 4, below.

The results are shown in FIG. 3. ANOVA indicated a significant electrostimulation effect (TE vs. sham), $F(1,16)=9.29$, $p<0.01$, and a significant drug effect (thiorphan vs. vehicle), $F(1,16)=29.54$, $p<0.01$. The group receiving both TE and thiorphan had a significantly greater percentage increase in tail flick latency than any of the other groups, $p<0.01$, according to Dunnett's Procedure.

EXAMPLE 5

Combined Effects of TE and i.p. Acetorphan—Analgesia

An experiment similar to that described in Example 4 was conducted with the systemically active enkephalinase inhibitor, acetorphan. The subjects were 84 male Sprague-Dawley rats weighing 180–220 grams. Each rat was implanted with ear electrodes under halothane anesthesia and subsequently habituated and pretested for tail flick latency as in Example 4. Forty-two rats then received i.p. injections of 15 mg/kg acetorphan (donated by J. C. Schwartz, INSERM, Paris) in a vehicle of ethanol (10%)/cremophor EL (10%)/saline (80%). Forty-two rats received the injection vehicle alone. Beginning five minutes after injection, half of the acetorphan recipients and half of the vehicle recipients received 30 min. of TE as in Example 4. The remaining half of each group received 30 min. of sham stimulation only. All rats were then immediately retested under "blind" conditions for tail flick latency and their analgesia scores were expressed as percentage increase from pretest to posttest latencies. These scores were analyzed by the same procedures employed in Example 4.

Figure 4:
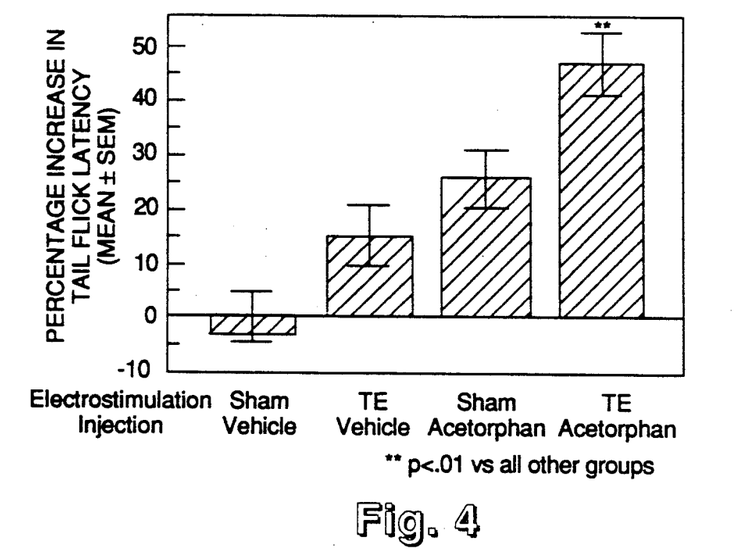
FIG. 4 is a bar graph showing the enhancement of TE-induced analgesia in rats by concomitant administration of acetorphan as described in Example 5, below.

The results are shown in FIG. 4. ANOVA indicated a significant electrostimulation effect (TE vs. sham), $F(1,80)=13.75$, $p<0.01$, and a significant drug effect (acetorphan vs. vehicle), $F(1,80)=31.93$, $p<0.01$. The group receiving both TE and acetorphan had a significantly greater percentage increase in tail flick latency than any of the other groups, $p<0.01$, according to Dunnett's Procedure.

EXAMPLE 6

Combined Effect of TE and L-tryptophan—Analgesia

Another experiment was conducted in which the neuroactive chemical promoter L-tryptophan, the amino acid precursor of serotonin, was administered concomitantly with transcranial electrostimulation as follows. The subjects were 40 male Sprague-Dawley rats, weighing 200–250 grams. Subjects were maintained on ad lib food and water and a 12 hour light/dark cycle. Four days prior to the experiment, each rat was placed under halothane anesthesia and implanted with gold-plated stainless steel electrodes through the apex of the anti-helix of each pinna as described in Example 2. On the three days preceding the experiment, each rat was habituated to a cylindrical plastic restrainer.

Each was placed in a restrainer and pretested for nociceptive sensitivity by measurement of tail flick latency on the 50° C. wet tail flick test (average of three trials). Each rat was then injected i.p. either with 200 mg/kg L-tryptophan in a vehicle of isotonic saline (95%)/2N HCL (5%) or with vehicle alone. This dose was selected on the basis of small pilot experiments. Beginning 40 minutes after injection, each rat was placed again in a restrainer, and the ear electrodes of each rat were connected to the stimulator through leads with a 200K ohm resistor in series. Twenty rats then received 30 minutes of TE stimulation (10 Hz, 10 µA, 2 msec pulse width), while twenty rats (the "sham stimulation group") received no stimulation. A 2×2 factorial design was employed so that ten rats received L-tryptophan and TE, ten rats received L-tryptophan and sham stimulation, ten rats received vehicle only and TE and ten rats received vehicle only and sham stimulation.

Immediately following TE or sham stimulation, all rats were retested under "blind" conditions for tail flick latency. Each animal's analgesia score was the percentage increase in tail flick latency from pretest to posttest. The results are set out in Table 2.

TABLE 2

COMBINED AND SEPARATE ANALGESIC EFFECTS OF TE AND L-TRYPTOPHAN: ANALGESIA SCORES (PER CENT CHANGE PRETEST TO POSTTEST) (MEAN ± SEM)

|  | TE | SHAM STIMULATION |
|---|---|---|
| L-TRYP i.p. | 65.4 ± 16.6* | −2.1 ± 4.2 |
| VEHICLE i.p. | 33.2 ± 9.8 | −5.0 ± 7.5 |

*p < .05 vs. all other groups (Dunnett's Test)

Two-way analysis of variance indicated a significant electrostimulation effect (TE vs. sham), $F(1,36)=25.42$, $p<0.01$, and a significant drug effect (L-tryptophan vs. vehicle), $F(1,36)=3.91$, $p<0.05$. The group receiving both TE and L-tryptophan had a significantly greater percentage increase in tail flick latency than any of the other groups, $p<0.05$, according to Dunnett's Procedure for post-hoc comparison of a single treatment group with all others.

EXAMPLE 7

Combined Effects of TE with D-phenylalanine and Tyrosine—Analgesia

The experiment described in Example 6 is repeated, substituting the amino acid D-phenylalanine or the amino acid D-tyrosine for the neuroactive chemical promoter L-tryptophan. A dosage of about 100 to about 500 mg of the amino acid per kg rat weight i.p. in saline is employed.

EXAMPLE 8

Combined Effects of TE with L-tryptophan and D-phenylalanine —Morphine Abstinence Syndrome An experiment in which the efficacy of the neuroactive chemical promoters D-phenylalanine and L-tryptophan in ameliorating the withdrawal symptoms of morphine addiction is conducted as follows. Rats are maintained as set out in Example 1 and electrodes are implanted and electronics set up as described in Example 2. However, while under anesthesia, the rats are implanted subcutaneously in the scapular region with Alzet (tm) osmotic minipumps filled with 20 mg/ml morphine sulfate dissolved in saline or with saline vehicle alone. The morphine-treated rats are rendered dependent by continuous infusion of 0.93 mg/kg/hr morphine sulfate for seven days. Abrupt abstinence is induced by removing the pumps under halothane anesthesia.

Twenty-four hours after pump removal, each rat receives 30 minutes of either sham stimulation as described in Example 1, electrostimulation as described in Example 2, or either L-tryptophan at the dosage level set out in Example 6 or D-phenylalanine at the dosage level set out in Example 7. Immediately after those treatments, the rats are placed in a clear plastic observation chamber with a grid floor and observed for 15 minutes under blind conditions on a standard checklist of opiate abstinence signs (wet dog shakes, genital licks, hind foot scratches, abdominal writhes, ptosis, dyspnea, diarrhea, and teeth chattering) as primarily based on Gianutsos, G., et al., "The Narcotic Withdrawal Syndrome in the Rat", in S. Ehrenpreis and A. Neidle (Eds.), Methods in Narcotic Research, New York: Marcel Dekker, pp. 293-310 (1975).

EXAMPLE 9

Combined Effects of TE and Acetorphan—Morphine Abstinence Syndrome

The experiment described in Example 8 is repeated either substituting the enkephalinase inhibitor acetorphan for the neuroactive chemical promoters L-tryptophan and D-phenylalanine or administering acetorphan in addition to those two amino acids. The same dosage regimen and vehicle described in Example 5 is employed.

EXAMPLE 10

Combined Effects of TE and Kelatorphin—Analgesia

The experiment described in Example 5 is repeated substituting the enkephalinase inhibitor kelatorphin for the neuroactive chemical promoter acetorphan. Kelatorphin is effective when given orally, consequently, the only change in the method set out in Example 5 is that the neuroactive chemical promoter is given orally in a suitable vehicle at a dosage of between approximately 25 and approximately, 200 mg/kg body weight.

EXAMPLE 11

Separate and Combined Effects of Transcranial Electrostimulation and Acetorphan with L-tryptophan, D-phenylalanine and B Complex Vitamins Analgesia can also be efficaciously induced with combinations of one or more neuractive chemical promoters and in combination with other substances. Using the protocols set out in Examples 3-5, humans are tested for the analgesic effect of such combinations as acetorphin and L-tryptophan, acetorphan and D-phenylalanine, acetorphan with L-tryptophan and a B vitamin such as niacinamide or vitamin $B_6$, acetorphan with D-phenylalanine and a B vitamin such as niacinamide or $B_{12}$ and so on, all concommitantly with TE. Dosage levels of the neuractive chemical promoters are as follows:

| L-tryptophan | about 50 mg, twice a day for a person weighing 75 kg |
|---|---|
| D-phenylalanine | between about 25 mg and about 125 mg given in two approximately equal doses per day for a person weighing 75 kg |
| acetorphan | about 1.6 mg per day for a person weighing 75 kg. |

Dosage levels of B vitamin(s) are on the order of 10-20 mg/kg body weight.

EXAMPLE 12

Combined Effects of Extended TE with Proglumide—Morphine Abstinence Syndrome

An experiment was performed to determine the separate and combined effects of TE and proglumide in rats addicted to morphine. Proglumide is an antagonist of the peptide neurohormone, cholecystokinin (CCK). CCK has been implicated as a contributing factor to narcotic tolerance and dependence. As an endogenous opioid antagonist, CCK might be expected to interfere with the actions of endorphins released by TE. Therefore, proglumide, by antagonizing CCK, might be expected to potentiate the effects of TE.

Thirty-two rats were rendered dependent by seven days subcutaneous infusion of 0.93 mg/kg/hr morphine sulfate via Alzet (tm) osmotic minipump as described in Example 9. The pumps were removed under light halothane anesthesia, initiating drug withdrawal. Twenty-four hours after pump removal, each animal was injected i.p. with either 10 mg/kg proglumide in saline or with saline alone and was given TE stimulation (10 Hz, 10 μA, 30 min.) or sham treatment as described in Example 2. Thus there were four groups: TE and proglumide, TE and saline, sham stimulation and proglumide, and sham stimulation alone. Each rat was then observed for 15 minutes on a standard checklist of opiate abstinence signs (wet-dog shakes, writhes, teeth chatter, ptosis etc.), again as described in Example 9.

Figure 5:
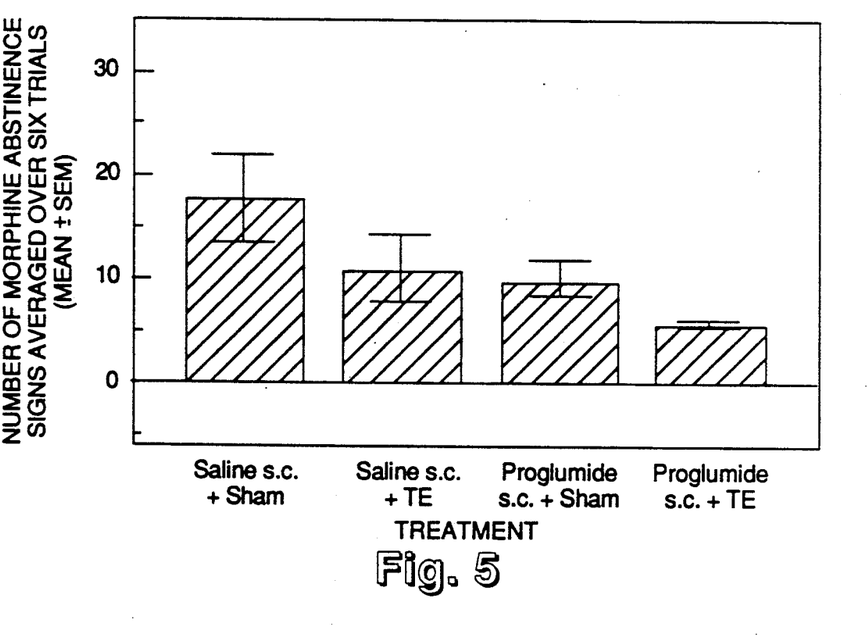
FIG. 5 is a bar graph showing the effect of concomitant administration of proglumide and TE in morphine addicted rats upon deprivation of morphine as described in Example 13, below.

The results are shown in FIG. 5. The group receiving both TE and proglumide (extreme right on the graph) had significantly fewer abstinence signs than any other group according to Dunnett's test for multiple comparisons with a single group.

EXAMPLE 13

Combined Effects of Extended TE with Proglumide—Morphine Abstinence Syndrome The experiment described in Example 12 may be extended wherein the drug-TE combination is given repeatedly at regular intervals over a 24 hour period. TE is given every three hours with the same parameters as set out in Example 12, and proglumide is administered as described in Example 12 just prior to each TE administration. The drug-TE combination is expected to produce fewer abstinence signs in the experimental subjects than would proglumide or TE given alone.

EXAMPLE 14

Combined Effects of TE and Pyrido [2,3-e]-as-Triazin Derivatives and Pharmaceutical Preparations Analgesia, sedation, narcosis potentiation, tetrabenzine antagonism and anti-phlogistic effects can be efficaciously induced with combined administration of TE as set out in examples 3-6 and pyrido[2,3-e]-as-triazine (PAT) derivatives of the following general formula wherein:

$R^1$ and $R^2$ each stand for a $C_{1-20}$alkylcarbonyl, halogenated ($C_{1-4}$alkyl)-carbonyl, $C_{1-4}$alkoxycarbonyl, benzoyl, phenyl-($C_{1-4}$alkyl)-carbonyl or phenyl-($C_{2-4}$alkenyl)carbonyl group or a 5-10-membered mono- or bicyclic nitrogen-containing heterocyclic acid residue (preferably a pyridylcarbonyl group) containing optionally one or more additional nitrogen, oxygen and/or sulfur atoms in the heterocyclic ring, and optionally one or more identical or different substituents selected from the group consisting of halogen, $C_{1-4}$ alkoxy, nitro and hydroxy are attached to the aromatic or heterocyclic rings, furthermore one of $R^1$ and $R^2$ may also stand for hydrogen atom, or $R^1$ and $R^2$ may form, together with the adjacent nitrogen atoms, a pyrazole-2,4 ring having optionally a $C_{1-6}$ alkyl substituent in position 3, and $R^3$ stands for hydrogen, halogen, $C_{1-4}$ alkoxy, amino, mono- ($C_{1-6}$ alkyl)-amino, di-($C_{1-6}$ alkyl)-amino, hydroxy, alkylated or acylated hydroxy, morpholino, peperazino, N-($C_{1-6}$ alkyl)-piperazino, N-benzylpiperazino or N-pyridylpiperazino group.

Pharmaceutically acceptable acid addition salts of PAT are prepared by acylating the respective 1,2 unsubstituted 1,2 dihydro-PAT derivatives. These substances are described in U.S. Pat. No. 4,324,786, incorporated herein by this specific reference to that patent.

The pharmaceutical preparations are for enteral or parental administration to warm-blooded animal(s) and contain the pharmacologically active ingredient alone or together with a pharmaceutically acceptable carrier. The dosage of the active ingredient depends on age, individual condition, method of administration and body weight. In normal patients, the estimated approximate dose in the case of oral administration is from 200 to 500 mg/kg of body weight.

EXAMPLE 15

Combined Effects of TE and Heteramino Benzofurans

Analgesia and anti-inflammatory effects can be efficaciously induced with combined administration of TE as set out in Examples 3-6 and heteramino benzofuran derivatives of the general formula in which $R_1$ represents hydrogen or an aliphatic radical, $R_2$ represents an amino group di-substituted by a divalent hydrocarbon radical, and the aromatic ring A may be additionally substituted, and their salts and/or isomers.

These substances are described in U.S. Pat. No. 4,451,462, which patent is incorporated herein by this specific reference thereto.

The pharmaceutical preparations are for enteral or parental administration to warm-blooded animal(s) and contain the pharmacologically active ingredient alone or together with a pharmaceutically acceptable carrier. The dosage of the active ingredient depends on age, individual condition, method of administration and body weight. In normal humans, the estimated approximate dose in the case of oral administration is from 2 to 10 mg/kg of body weight.

EXAMPLE 16

Combined Effects of TE and Isochromans

Antipsychotic and hypotensive effects can be efficaciously induced with combined administration of TE and amino derivatives of isochromans of the general formula given in U.S. Pat. No. 4,487,774, incorporated herein by this specific reference to that patent.

The pharmaceutical preparations are for enteral or parental administration to warm-blooded animal(s) and contain the pharmacologically active ingredient alone or together with a pharmaceutically acceptable carrier. The dosage of the active ingredient depends on age, individual condition, method of administration and body weight. In normal humans, the estimated approximate dose in the case of oral administration is from 2 to 10 mg/kg of body weigh.

EXAMPLE 17

Combined Effects of TE with L-Tryptophan and Acetorphan—Analgesia

The combined effects of administration of TE together with both the amino acid L-tryptophan and the enkephalinase inhibitor acetorphan are assessed as follows. Rats are maintained in accordance with the protocols set out in Example 3, and tested for the combined effects of TE and these neuroactive chemical promoters using the tail flick latency model described in that same example. TE is given as set out in Example 4 and acetorphan dosages are the same as set out in Example 4. In addition, L-tryptophan is administered to the rats in the dosages described in Example 5. It is expected that the results seen in both Examples 4 and 5 as described above will be even more dramatic when both neuroactive chemical promoters are administered concurrently with TE.

EXAMPLE 18

Effect of TE on Analgesia

The 80 subjects participating in this study all had intractable low back pain. This type of pain limits musculo-skeletan output, and is therefore subject to a more objective measurement of the analgesic measures which may be applied. An isokinetic, automated exercise device (Kin-Com TM) was used to test the subjects' ability to output musculo-skeletal torque before and after administration of TE. Because of the varying nature of each subjecdt's pain, the ability to trigger pain in each subject, each subject's idiosyncratic use of drugs, and each subject's differing physical condition, an experimental design was implemented in which each subject served as his own control.

Volunteering subjects were randomized into two matched groups. Each subject participated in a 2×2 cross-over design in which he received two randomly assigned analgesic treatments and two sham treatments (placebos). The analgesic treatment was application of low current, transcranial electrostimulation therapy (TE).

Subjects were tested on the Kin-Com every fourth day. The tests were performed at two different angular velocities, 15 and 30 degrees/sec. Each subject was challenged in eccentric (muscle relaxing) and concentric (muscles contracting) modes. These tests were conducted pre- and post-TE. Results showed significant differences between treatment days and significant differences in two of four days between treatment and sham administration of Te.

EXAMPLE 19

Effect of TE to Relieve Nicotine Withdrawals Symptoms—Smoking Cessation

Transcranial electrostimulation (TE) has been applied in double blind clinical trials to long term smokers (at least one pack per day) who indicated they wished to quit smoking. Three different protocols were investigated—one treatment per day for eight days, two treatments per day for five days, or one treatment per day combined with a behavior modification program. In the former protocol, treatments were given Monday through Friday and then the following Monday through Wednesday. In the second protocol, treatments were delivered Monday through Friday. The behavior modification program used in the third protocol was applied in the recognition that TE served to assist in overcoming short term withdrawal symptoms, but that physiological craving required address by behavior modification to induce long term support against recidivism.

The subjects selected for participation in the study smoked at least one pack of cigarettes per day for at least five years were between the ages of 18 and 55, were not pregnant, had no known threatening medical conditions, and had tested negative for cannaboids and other confounding drugs. At a pre-study orientation, the subjects supplied information on the base cigarette count and brand of cigarette smoked and were prospectively randomized into two groups—treatment and placebo.

TE consisted of low current (less than 40 $\mu$A), pulsed signals delivered through electrodes attached to the earlobes. The stimulus was delivered below perception levels of the subjects. The duration of each treatment was approximately one hour.

Subjects provided a daily record of the number of cigarettes and the time that they smoked, and completed questionaires to assess withdrawal symptoms. Saliva samples were collected at the clinic from each subject at orientation before the study began and on each day of treatment. Cotinine levels were determined using a monoclonal antibody enzyme linked immunosorbent assay (ELISA).

Additionally, the Shiffman Withdrawal Scale, Analog Craving Scale and an instrument to assess withdrawal symptom were administered regularly throughout the study. Subjects provided urine samples at orientation and on demand during the study. These samples were assayed to detect marijuana, cocaine or other drugs whose use could confound the analysis of study results. Subjects whose drug test was positive were excluded from the study.

Sixty-seven (67) subjects participated in the trial administering one treatment per day. Of these, 40 received actual treatment and 27 received placebo (no current). The quit rates verified by salivary continine analysis were 55 percent in the treatment group and 22 percent in the placebo group.

Forty-one (41) subjects participated in the two treatment per day trial. Twenty-five received actual treatment and 16 received placebo. The quit rates were 68 percent and 38 percent respectively.

The subjects involved in the third protocol were randomly assigned to one of four groups: treatment+behavior modification, treatment only behavior modification was promised after the initial experimental period), behavior modification only (treatment was promised after the initial experimental period), and placebo+behavior modification. The group which received treatement+behavior modification had a statistically significant greater quit rate than the other three groups.

EXAMPLE 20

Separate and Combined Effects of Transcranial Electrostimulation and Acetorphan, with L-tryptophan, D-phenylalanine, B Complex Vitamins and Nicotinic Acid The experiment described in Example 11 can be repeated using additional chemical promoters which assist the synthesis, inhibit the degradation, and facilitate uptake, distribution and metabolism of neuroactive substances. Nicotinic acid in the form of niacinamide (50 mg given once per day), vitamin $B_6$, peridoxin (50 mg given once per day) and monoamine oxidase inhibitors such as D-L-phenylalanine (500 mg given once per day), L-glutamine, or pyridoxal-5-phosphate (10 mg given once per day) assist in producing enhanced analgesic effects.

EXAMPLE 21

Combined Effect of TE and Lorglumide —Analgesia

An experiment was conducted in which the neuroactive chemical promoter lorglumide, a cholecystrokinin antagonist, was used to enhance relief from painful stimuli by repeating the protocol described in Example 6 above. The 49 rats were pretested for response latency in the 50° C. wet-tail flick test and injected with 1.5 mg/kg lorglumide i.p. or saline alone. Half of the group then received TE (10 $\mu$A, 10 Hz, 2 msec pulse width), while the other half received "sham stimulation". Following the 30 minutes f stimulation (or sham stimulation), each rat was retested for tail flick latency. Each animal's analgesia score was recorded as the percentage increase in tail flick latency from pretest to posttest. The results are set out in Table 3.

TABLE 3

| Combined and Separate Analgesic Effects of TE and Lorglumide: Analgesia Scores (Percent Change Pre test to Posttest) (Mean ± SEM) | | |
|---|---|---|
| | TE | Sham Stimulation |
| lorglumide i.p. | 72.7 ± 19.7* | 1.5 ± 7.1 |
| vehicle i.p. | 23.4 ± 6.9 | 3.3 ± 12.0 |

*p < .05 vs. all other groups (Dunnett's Test)

The group receiving both TE and lorglumide had a significantly greater percentage increase in tail flick latency than any of the other groups, p<0.05, according to Dunnett's Procedure for post-hoc comparison of a single treatment group with all others.

EXAMPLE 22

Combined Effect of TE and Proglumide —Analgesia

An experiment was conducted in which the neuroactive chemical promoter proglumide, a cholecystokinin antagonist, was used to enhance relief from painful stimuli by repeating the protocol described in Example 6 above. The 44 rats were pretested for response latency in the 50° C. wet-tail flick test and injected with 10 mg/kg proglumide i.p. or saline alone. Half of the group then received TE (10 $\mu$A, 10 Hz, 2 msec pulse width), while the other half received "sham stimulation". Following the 30 minutes of stimulation (or sham stimulation), each rat was retested for tail flick latency. Each animal's analgesia score was the percentage increase in tail flick latency from pretest to posttest. The results are set out in Table 4.

TABLE 4

Combined and Separate Analgesic Effects of TE and Proglumide: Analgesia Scores (Percent Change Pretest and Posttest) (Mean ± SEM)

|  | TE | Sham Stimulation |
|---|---|---|
| proglumide i.p. | 60.2 ± 10.3 | −90.0 ± 9.5 |
| vehicle i.p. | 23.0 ± 6.5 | 1.8 ± 10.1 |

*p < .05 vs. all other groups (Dunnett's Test)

The group receiving both TE and proglumide had a significantly greater percentage increase in tail flick latency than any of the other groups, $p<0.05$, according to Dunnett's Procedure for post-hoc comparison of a single treatment group with all others.

Although described in terms of the above presently preferred embodiments, it will be recognized by those skilled in the art who have the benefit of this disclosure that changes can be made to the dosages, protocols, current levels, and so on as set out in those examples without departing from the spirit and scope of the present invention. All such changes are intended to fall within the scope of the following claims.

What is claimed is:

1. A method of enhancing the relief from painful, stressful, or painful and stressful stimuli provided by transcranial electrostimulation comprising the concomitant administration of a neuroactive chemical promoter and transcranial electrostimulation to an animal experiencing a stressful or painful condition.

2. The method of claim 1 wherein the neuroactive chemical promoter is an indoleamine, catchecholamine, amino acid present in the central nervous system, amino acid or peptide capable of inducing a central nervous system response, combination of amino acids, combination of amino acids with an aspirin-like drug, cholinergic of amino acids with an aspirin-like drug, cholinergic agent, peptide capable of inducing a central nervous system response, or a precursor or synthetic derivative of same, an inhibitor of one of the enzymes active in the metabolic pathways involved in producing or degrading same, an antagonist or binding competitor of same, and combinations of same.

3. The method of claim 1 wherein the neuroactive chemical promoter is an enzyme active in the metabolic pathway of peptidyl opiates, a tryptamine derivative, an enzyme active in the metabolic pathway involved in making tryptamine derivatives, an amino acid, a peptide which is a modulator of the central nervous system, or an antagonist of a peptide which is a modulator of the central nervous system.

4. The method of claim 1 wherein the neuroactive chemical promoter is selected from the group consisting of lorglumide proglumide, 5-hydroxy-dl-tryptophan, acetorphan, thiorphan, or L-tryptophan.

5. The method of claim 1 wherein the current of the transcranial electrostimulation is between approximately 5 and approximately 40 µA.

6. The method of claim 1 wherein the pulse width of the transcranial electrostimulation is between approximately 0.1 and approximately 8.0 msec.

7. The method of claim 1 wherein the frequency of the transcranial electrostimulation is between approximately 5 and approximately 50 Hz.

8. The method of claim 1 wherein the duration of the transcranial electrostimulation is between approximately 10 and approximately 60 minutes.

9. A method of enhancing the effects of the neuroactive substances that modulate neurohumoral mechanisms in a living being comprising administering transcranial electrostimulation concomitantly with a neuroactive chemical promoter.

10. The method of claim 9 wherein the neuroactive chemical promoter is a neuroactive substance found in the brain or central nervous system of the living being.

11. The method of claim 9 wherein the neuroactive chemical promoter is an amino acid, an inhibitor of the enzymes active in the metabolic pathways involved in production or degradation of an opioid peptide, an indoleamine, or an antagonist or binding competitor of an endogenous peptide found in the central nervous system of the living being.

12. The method of claim 9 wherein the neuroactive chemical promoter is selected from the group consisting of acetorphin, kelatorphin or thiorphan.

13. The method of claim 9 wherein the neuroactive chemical promoter is selected from the group consisting of L-tryptophan, 5-hydroxy-dl-tryptophan, tyrosine, or D-phenylalanine.

14. A method of remediating imbalances or deficiencies in the neuroactive substances that modulate neurohumoral mechanisms in a living being comprising the concomitant administration of a neuroactive chemical promoter and transcranial electrostimulation to an animal.

15. The method of claim 14 wherein the neuroactive chemical promoter is selected from the group consisting of:

precursors or synthetic derivates of endorphine, enkephalins, or dynorphins, inhibitors of the enzymes active in the metabolic pathways involved in producing or degrading endorphins, enkephalins, or dynorphins, and binding competitors or antagonists of endorphins, enkephalins, or dynorphins, amino acids present in the central nervous system or capable of inducing a central nervous system response, inhibitors of the enzymes active in the metabolic pathways involved in producing or degrading such amino acids, and antagonists or binding competitors of such amino acids, peptides present in the central nervous system or capable of inducing a central nervous system response, enzymes active in the metabolic pathways involved in producing or degrading such peptides, inhibitors of the enzymes involved in producing or degrading such peptides, and antagonists or binding competitors of such peptides, and indoleamines, cholinergic agents, or catecholamines, enzymes active in the metabolic pathways involved in producing and degrading indoleamines, cholinergic agents, or catecholamines, precursors of indoleamines, cholinergic agents, or catecholamines, inhibitors of the enzymes involved in producing or degrading indoleamines, cholinergic agents, or catecholamines, and antagonists or binding competitors of indoleamines, cholinergic agents, or catecholamines.

16. The method of claim 14 wherein the neuroactive chemical promoter is proglumide, lorglumide 5-hydroxy-di-tryptophan, acetorphan, thiorphan, L-tryptophan or combinations of proglumide, lorglumide 5-hydroxy-dl-tryptophan, acetorphan, thiorphan, and L-tryptophan.

17. The method of claim 14 additionally comprising the concomitant administration of a second neuroactive chemical promoter.

18. A method of inducing analgesia in a patient comprising the concomitant administration of transcranial electrostimulation and L-tryptophan or 5-hydroxy-dl-tryptophan.

19. A method of inducing analgesia in a patient comprising the concomitant administration of transcranial electrostimulation and acetorphan, thiorphan lorglumide or proglumide.

20. A method of relieving the symptoms of withdrawal from drug addiction comprising the concomitant administration of transcranial electro-stimulation and L-tryptophan or 5-hydroxy-dl-tryptophan to a living being addicted to a drug upon deprivation of the drug.

21. A method of relieving the symptoms of withdrawal from drug addiction comprising the concomitant administration of transcranial electrostimulation and acetorphan, thiorphan lorglumide or proglumide to a living being addicted to a drug upon deprivation of the drug.

22. A method of treating a mammal for relief of painful or stressful stimuli or for relief of painful and stressful stimuli comprising the concomitant administration to a mammal of a neuroactive chemical promoter and transcranial electrostimulation utilizing charge-balanced, biphasic electrical current at an amplitude of from about 5 to about 40 $\mu$A having a pulse width of from about 0.1 to about 8.0 msec and a frequency from about 5 to about 50 Hz.

23. The method of claim 22 wherein the neuroactive chemical promoter is an indoleamine, catecholamine, amino acid present in the central nervous system, amino acid capable of inducing a central nervous system response, cholinergic agent, peptide capable of inducing a central nervous system response, a precursor, antagonist, or binding competitor of a neurotransmitter, inhibitor of an enzyme active in a metabolic pathway involved in producing or degrading same, and combinations of same.

24. The method of claim 22 wherein the neuroactive chemical promoter is selected from the group consisting of proglumide, lorglumide, 5-hydroxy-dl-tryptophan, acetorphan, thiorphan, or L-tryptophan, or combinations of same.

25. The method of claim 22 wherein the duration of the transcranial electrostimulation is between about 10 and about 60 minutes.

26. The method of claim 22 wherein the transcranial electrostimulation is administrated through electrodes affixed to a low impedance site on the external ear of the mammal.

27. The method of claim 22 wherein the electrical current of the transcranial electrostimulation is administered using generally rectangular waveforms.

* * * * *